US00PP13173P2

(12) United States Plant Patent
Mislow, III

(10) Patent No.: US PP13,173 P2
(45) Date of Patent: Nov. 5, 2002

(54) FICUS PLANT NAMED '000-G1'

(75) Inventor: Gregory John Mislow, III, Miami, FL (US)

(73) Assignee: Rose of Sharon Nursery Inc., Miami, FL (US)

( * ) Notice: Subject to any disclaimer, the term of this patent is extended or adjusted under 35 U.S.C. 154(b) by 0 days.

(21) Appl. No.: 10/004,779

(22) Filed: Dec. 7, 2001

(51) Int. Cl.[7] ..... A01H 5/00

(52) U.S. Cl. ..... Plt./211

(58) Field of Search ..... Plt./211

*Primary Examiner*—Kent L. Bell
(74) *Attorney, Agent, or Firm*—C. A. Whealy

(57) ABSTRACT

A distinct cultivar of Ficus plant named '000-G1', characterized by its mostly upright habit when grown under full sun conditions and upright and outwardly spreading habit when grown under shade conditions; freely branching habit, full and dense plants; glossy variegated leaves; and undulate foliage.

2 Drawing Sheets

BOTANICAL CLASSIFICATION/CULTIVAR DENOMINATION

*Ficus benjamina* cultivar '000-G1'.

BACKGROUND OF THE INVENTION

The present Invention relates to a new and distinct cultivar of Ficus plant, botanically known as *Ficus benjamina* and hereinafter referred to by the name '000-G1'.

The new Ficus was discovered by the Inventor in June, 1999, in a controlled environment in Miami, Fla., as a naturally-occurring branch mutation of an unidentified selection of *Ficus benjamina,* not patented. The new Ficus was selected on the basis of its undulate variegated foliage.

Asexual propagation of the new cultivar by cuttings since February, 2000, in a controlled environment in Miami, Fla., has shown that the unique features of this new Ficus are stable and reproduced true to type in successive generations.

SUMMARY OF THE INVENTION

The following traits have been repeatedly observed and are determined to be the unique characteristics of '000-G1'. These characteristics in combination distinguish '000-G1' as a new and distinct cultivar:

1. Mostly upright when grown under full sun conditions and upright and outwardly spreading when grown under shade conditions.

2. Freely branching habit, full and dense plants.

3. Glossy variegated leaves.

4. Undulate foliage.

In side-by-side comparisons conducted by the Inventor in Miami, Fla., plants of the new Ficus differed from plants of the parent, the unidentified selection of *Ficus benjamina,* in the following characteristics:

1. Plants of the new Ficus had smaller leaves than plants of the parent selection.

2. Fully expanded leaves of plants of the new Ficus were variable in size and shape whereas fully expanded leaves of plants of the parent selection were uniform in size and shape.

3. Leaves of plants of the new Ficus were undulate whereas leaves of plants of the parent selection were not undulate.

4. Leaves of plants of the new Ficus were variegated whereas leaves of plants of the parent selection were not variegated.

5. Woody stems of plants of the new Ficus were smoother than woody stems of plants of the parent selection.

Plants of the new Ficus can be compared to plants of the Ficus cultivar 'Monique', not patented. In side-by-side comparisons conducted by the Inventor in Miami, Fla., plants of the new Ficus differed from plants of the cultivar 'Monique' in the following characteristics:

1. Fully expanded leaves of plants of the new Ficus were variable in size and shape whereas fully expanded leaves of plants of the cultivar 'Monique' were uniform in size and shape.

2. Leaves of plants of the new Ficus were variegated whereas leaves of plants of the cultivar 'Monique' were not variegated.

BRIEF DESCRIPTION OF THE PHOTOGRAPHS

The accompanying colored photographs illustrate the overall appearance of the new Ficus, showing the colors as true as it is reasonably possible to obtain in colored reproductions of this type. Colors in the photographs may differ slightly from the color values cited in the detailed botanical description which accurately describe the colors of the new Ficus.

The photograph on the first sheet comprises a side perspective view of a typical plant of '000-G1' grown under full sun conditions.

The photograph at the top of the second sheet comprises a side perspective view of a typical plant of '000-G1' grown under 60 to 90% polypropylene shadecloth.

The photograph at the bottom of the second sheet comprises a close-up view of typical leaves of the new Ficus.

DETAILED BOTANICAL DESCRIPTION

The cultivar '000-G1' has not been observed under all possible environmental conditions. The phenotype may vary somewhat with variations in environment such as temperature and light intensity without, however, any variance in genotype.

The aforementioned photographs and following observations and measurements describe plants of the new Ficus that were grown in an outdoor nursery in Miami, Fla. One group of plants were grown in 35.5-cm containers and under full sun conditions. Another group of plants were grown in 25.5-cm containers and under 60 to 90% polypropylene shadecloth conditions. During the production of the plants, day temperatures averaged about 85° F. and night temperatures averaged about 75° F. Plants used for the photographs and description were about 18 months from planting. Color references are made to The Royal Horticultural Society Colour Chart, version 1995, except where general terms of ordinary dictionary significance are used.

Botanical classification: *Ficus benjamina* cultivar '000-G1'.

Parentage: Naturally-occurring branch mutation of an unidentified selection of *Ficus benjamina,* not patented.

Propagation:

*Type*.—By cuttings.

*Time to initiate roots*.—Summer: About 14 days at 75° F. Winter: About 21 to 30 days at 55 to 60° F.

*Time to produce a rooted plant*.—Summer: About 40 to 45 days at 75° F. Winter: About 45 to 60 days at 55 to 60° F.

*Root description*.—Fibrous and freely-branching.

Plant description:

*Appearance*.—Plants grown under full sun conditions were mostly upright. Plants grown under 60 to 90% shade conditions were upright and outwardly spreading. Freely branching habit give plants a very fully and dense appearance. Plants resist leaf drop. Appropriate for 25.5 to 35.5-cm containers.

*Growth rate/vigor*.—Vigorous, relatively rapid growth rate.

*Plant height*.—Plants grown under full sun conditions: About 160 cm. Plants grown under 60 to 90% shade conditions: About 140 cm.

*Plant width*.—Plants grown under full sun conditions: About 80 cm. Plant grown under 60 to 90% shade conditions: About 120 cm.

*Branching habit, plants grown under full sun and 60 to 90% shade*.—Freely branching habit; plants typically produce one lateral branch at every node; full and dense plants.

*Lateral branches*.—Length, lower branches: Plants grown under full sun conditions: About 80 cm. Plants grown under 60 to 90% shade conditions: About 110 cm. Diameter, lower branches: Plants grown under full sun conditions: About 1.5 cm. Plants grown under 60 to 90% shade conditions: About 1 cm. Internode length: Plants grown under full sun conditions: About 2 cm. Plants grown under 60 to 90% shade conditions: About 3 cm. Texture, plants grown under full sun and 60 to 90% shade: Older branches: Woody, glabrous. Young branches: Smooth. Lenticels, plants grown under full sun and 60 to 90% shade: Location/arrangement: Prominent on older, woody branches; horizontally orientated; about 1 to 3 mm apart. Size: About 5 mm by 1 mm. Color: Close to 200C to 200D. Color: Immature, plants grown under full sun and 60 to 90% shade: Closest to, but darker than 148A. Main branches, woody: Plants grown under full sun conditions: Close to 196A. Plants grown under 60 to 90% shade conditions: Closest to 199B to 199C.

*Foliage description, leaves of plants grown under full sun and 60 to 90% shade are variable in shape and size*.—Length: Plants grown under full sun conditions: About 5.4 cm. Plants grown under 60 to 90% shade conditions: About 1.8 cm. Width: Plants grown under full sun conditions: About 7.1 cm. Plants grown under 60 to 90% shade conditions: About 2.4 cm. Shape, plants grown under full sun and 60 to 90% shade: Roughly elliptic; apex, elongated acuminate; base, cuneate; margin, entire and undulating. Orientation and aspect, plants grown under full sun and 60 to 90% shade: Slightly concave and undulating. Texture, plants grown under full sun and 60 to 90% shade: Mostly smooth, slightly rugose; glabrous; thick and leathery. Color, plants grown under full sun and 60 to 90% shade: Young leaves, upper surface: Center, irregular in shape and size, more green than 147A. Surrounding central area to margins, closest to 146A; glossy. Young leaves, lower surface: More green than 146A; glossy. Fully expanded leaves, upper surface: Center, irregular in shape and size, darker green than 147A. Surrounding central area to margins, more green than 146A; glossy. Fully expanded leaves, lower surface: Between 146A and 147A; glossy. Venation, upper surface: More green than 146A. Venation, lower surface: Close to 150D. Petiole, plants grown under full sun and 60 to 90% shade: Length: About 1.1 cm. Diameter: Less than 1 mm. Strength: Strong, wiry. Color: 146A.

Flower description: Flower development has not been observed on plants of the new Ficus grown under commercial production conditions.

Disease/pest resistance: Plants of the new Ficus have not been observed to be resistant to pathogens or pests common to Ficus.

Weather tolerance: Plants of the new Ficus have been observed to be tolerant to wind, rain and temperatures ranging from 35 to 100° F.

It is claimed:

1. A new and distinct cultivar of Ficus plant named '000-G1', as illustrated and described.

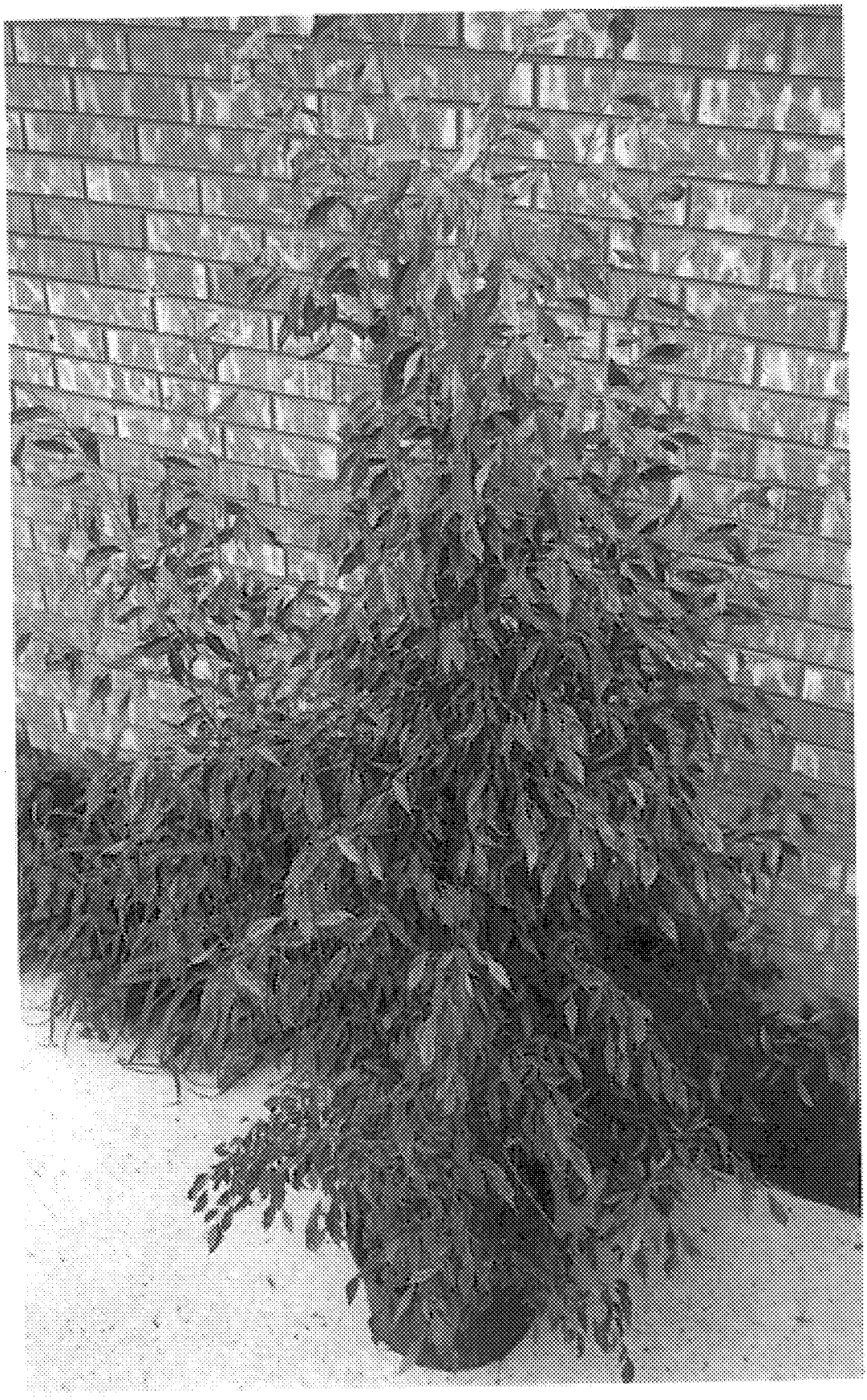

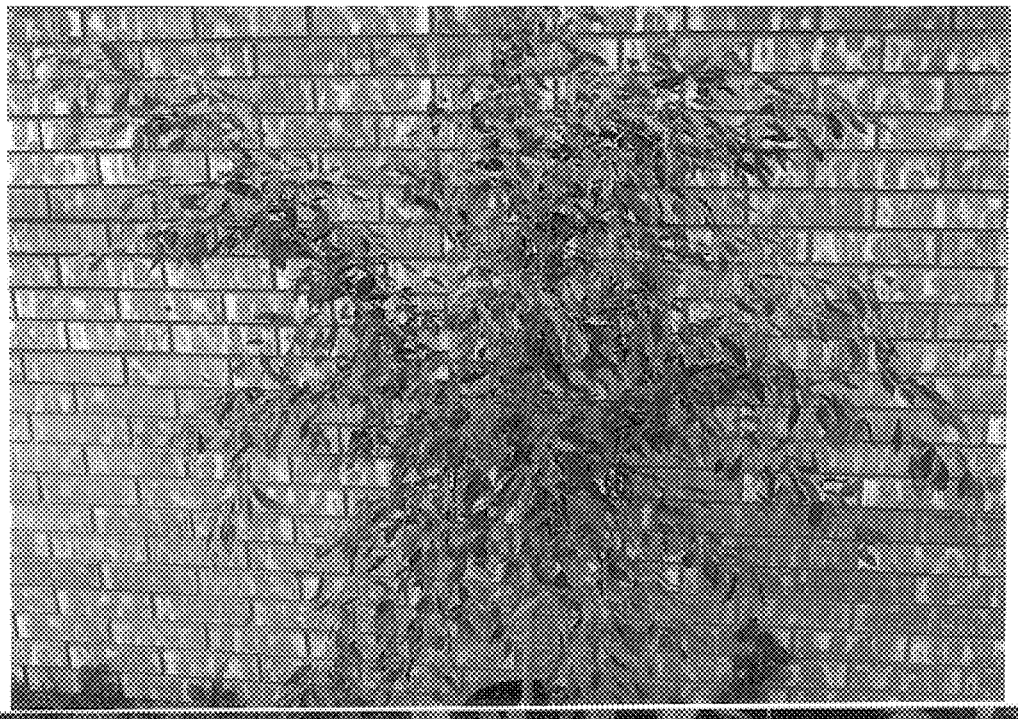
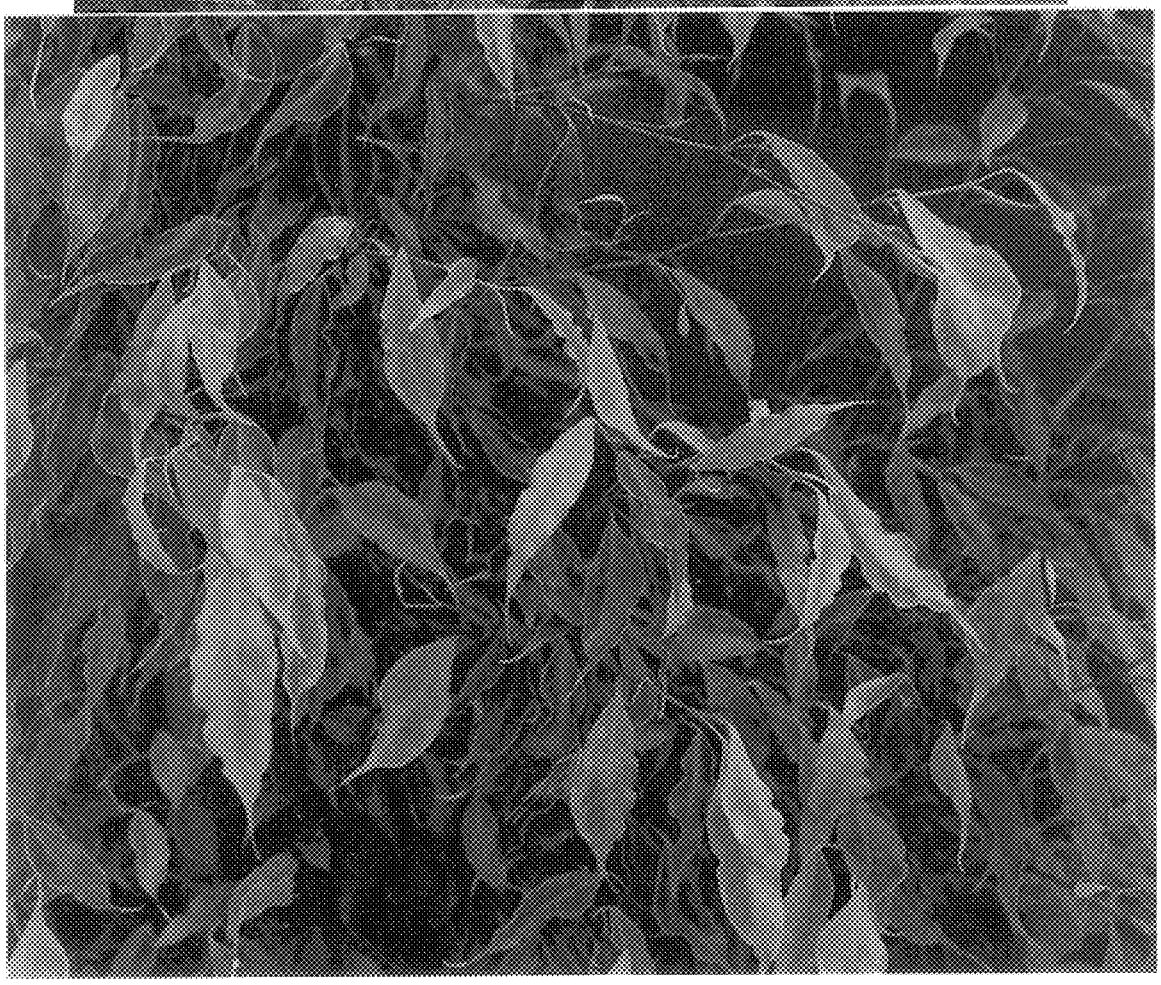

* * * * *